(12) United States Patent
Govari

(10) Patent No.: US 10,045,707 B2
(45) Date of Patent: Aug. 14, 2018

(54) BASKET CATHETER WITH FAR-FIELD ELECTRODE

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/451,742

(22) Filed: Mar. 7, 2017

(65) Prior Publication Data

US 2017/0172442 A1 Jun. 22, 2017

Related U.S. Application Data

(63) Continuation of application No. 14/616,811, filed on Feb. 9, 2015, now Pat. No. 9,833,161.

(51) Int. Cl.
*A61B 5/042* (2006.01)
*A61B 5/00* (2006.01)
*A61B 18/14* (2006.01)
*A61B 5/06* (2006.01)
*A61B 18/00* (2006.01)

(52) U.S. Cl.
CPC .......... *A61B 5/0422* (2013.01); *A61B 5/6858* (2013.01); *A61B 5/6859* (2013.01); *A61B 5/7203* (2013.01); *A61B 18/1492* (2013.01); *A61B 5/065* (2013.01); *A61B 2018/00267* (2013.01); *A61B 2018/00357* (2013.01); *A61B 2018/00577* (2013.01)

(58) Field of Classification Search
CPC ............................ A61B 5/0422; A61B 5/6958
See application file for complete search history.

(56) References Cited

U.S. PATENT DOCUMENTS

| 5,546,951 A | 8/1996 | Ben Haim |
| 5,738,096 A | 4/1998 | Ben Haim |

(Continued)

FOREIGN PATENT DOCUMENTS

| EP | 1 169 973 A1 | 1/2002 |
| EP | 1 319 364 A2 | 6/2003 |

(Continued)

OTHER PUBLICATIONS

European Search Report dated Apr. 26, 2016 from corresponding European Patent Application No. 16154609.8.

(Continued)

*Primary Examiner* — Lee S Cohen

(57) ABSTRACT

Cardiac catheterization is performed with a catheter having a basket-shaped assembly at its distal end. A plurality of spline electrodes are disposed on the splines of the assembly. The assembly is configurable in an expanded arrangement wherein the splines bow radially outwardly and in a collapsed arrangement, wherein the splines are arranged generally along the longitudinal axis of the catheter body. A far-field electrode is disposed in the interior of the assembly. An intracardiac electrogram and a far-field electrogram are obtained with at least one of the spline electrodes and the far-field electrode, respectively. The far-field component is removed from the intracardiac electrogram using the far-field electrogram.

10 Claims, 3 Drawing Sheets

(56) References Cited

U.S. PATENT DOCUMENTS

| | | |
|---|---|---|
| 5,772,590 A | 6/1998 | Webster, Jr. |
| 5,860,974 A | 1/1999 | Abele |
| 6,004,269 A | 12/1999 | Crowley et al. |
| 6,014,579 A | 1/2000 | Pomeranz et al. |
| 6,064,905 A | 5/2000 | Webster, Jr. et al. |
| 6,226,542 B1 | 5/2001 | Reisfeld |
| 6,236,883 B1 | 5/2001 | Ciaccio et al. |
| 6,240,307 B1 | 5/2001 | Beatty et al. |
| 6,301,496 B1 | 10/2001 | Reisfeld |
| 6,669,692 B1 | 12/2003 | Nelson et al. |
| 6,690,963 B2 | 2/2004 | Ben Haim et al. |
| 6,748,255 B2 | 6/2004 | Fuimaono et al. |
| 6,814,733 B2 | 11/2004 | Schwartz et al. |
| 6,892,091 B1 | 5/2005 | Ben Haim et al. |
| 6,997,924 B2 | 2/2006 | Schwartz et al. |
| 7,156,816 B2 | 1/2007 | Schwartz et al. |
| 7,245,962 B2 | 7/2007 | Ciaccio et al. |
| 7,536,218 B2 | 5/2009 | Govari et al. |
| 7,756,576 B2 | 7/2010 | Levin |
| 9,078,583 B2 | 7/2015 | Nguyen et al. |
| 9,380,953 B2 | 7/2016 | Houben et al. |
| 9,421,061 B2 | 8/2016 | Ben Zriham et al. |
| 9,554,718 B2 | 1/2017 | Bar-Tal |
| 2009/0099468 A1 | 4/2009 | Thiagalingam et al. |
| 2013/0019945 A1 | 1/2013 | Hekmatshoar-Tabari et al. |
| 2013/0211510 A1 | 8/2013 | Lederman et al. |
| 2013/0281870 A1 | 10/2013 | El Haddad et al. |
| 2013/0345583 A1 | 12/2013 | Thakur et al. |
| 2014/0005664 A1 | 1/2014 | Govari et al. |
| 2014/0081114 A1 | 3/2014 | Shachar et al. |
| 2014/0128709 A1 | 5/2014 | Kordis et al. |
| 2014/0180151 A1 | 6/2014 | Maskara et al. |
| 2014/0187991 A1 | 7/2014 | Thakur et al. |
| 2014/0257069 A1 | 9/2014 | Eliason et al. |
| 2015/0313491 A1 | 11/2015 | Edwards et al. |

FOREIGN PATENT DOCUMENTS

| | | | |
|---|---|---|---|
| WO | WO 96/05768 A1 | | 2/1996 |
| WO | WO 2016/044687 | * | 3/2016 |

OTHER PUBLICATIONS

U.S. Appl. No. 62/093,733, filed Dec. 18, 2014.
European Examination Report dated Mar. 23, 2017 from corresponding European Patent Application No. 16154609.8.

* cited by examiner

BASKET CATHETER WITH FAR-FIELD ELECTRODE

CROSS REFERENCE TO RELATED APPLICATIONS

This application is a continuation of U.S. patent application Ser. No. 14/616,811, filed Feb. 9, 2015, now U.S. Pat. No. 9,833,161, the entire contents of which is incorporated herein by reference.

BACKGROUND OF THE INVENTION

Field of the Invention

This invention relates to medical instruments adapted for introduction into the body. More particularly this invention relates to medical instruments having electrodes for obtaining cardiac electrograms.

Description of the Related Art

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time. Various electrode designs are known for different purposes. In particular, catheters having basket-shaped electrode arrays are known and described, for example, in U.S. Pat. No. 5,772,590, the disclosure of which is incorporated herein by reference.

Sensors in a cardiac chamber may detect far-field electrical activity, i.e., the ambient electrical activity originating away from the sensors, which can distort or obscure local electrical activity, i.e., signals originating at or near the sensor location. Commonly assigned U.S. Patent Application Publication No. 2014/0005664 of Govari et al., which is herein incorporated by reference, discloses distinguishing a local component in an intracardiac electrode signal, due to the tissue with which the electrode is in contact from a remote-field contribution to the signal, and explains that a therapeutic procedure applied to the tissue can be controlled responsively to the distinguished local component.

Commonly assigned U.S. Pat. No. 6,748,255 to Fuimaono et al., the disclosure of which is herein incorporated by reference, describes a basket catheter for mapping the heart. The catheter comprises an elongated catheter body and at least one lumen therethrough. A basket-shaped electrode assembly is mounted at the distal end of the catheter body. The basket assembly comprises a plurality of splines connected at their proximal and distal ends. Each spine comprises at least one electrode. The basket assembly has an expanded arrangement wherein the splines bow radially outwardly and a collapsed arrangement wherein the splines are arranged generally along the axis of the catheter body. The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the splines of the basket-shaped mapping assembly to find the positions of the at least one electrode of each spine.

SUMMARY OF THE INVENTION

In the expanded form of a basket catheter, the electrodes of the spline contact the surface of the heart and acquire signals corresponding to electropotentials generated at their points of contact with the surface. However, since the spline electrodes are in a conductive medium (the blood), in addition to the electropotentials from the point of contact the acquired signals also include potential components from other regions of the heart. These potential components are termed far-field components. The basket catheter is provided with a contraction wire, which used to collapse the catheter from an expanded basket shape into a contracted shape, in which its splines are relatively close together.

The far-field components constitute an interfering signal on the surface electropotentials. To counteract the interference, embodiments of the present invention position an electrode that senses far-field components, termed herein a "far-field electrode", on the contraction wire of the catheter.

In the expanded configuration of the catheter, the far-field electrode is located on the contraction wire so as to be approximately equidistant from all the spline electrodes, and is prevented from contacting the surface of the heart by the splines. The far-field electrode is physically removed from the endocardial surface, and thus acquires a signal only from the far-field, and this signal is subtracted from the signals acquired by the spline electrodes so as to counteract the interference suffered by these electrodes.

There is provided according to embodiments of the invention an apparatus including a catheter having an elongated catheter body, and a basket-shaped assembly at the distal end of the catheter body. The basket-shaped assembly has a plurality of splines connected at its proximal extremity and its distal extremity, and a plurality of spline electrodes disposed on the splines. The basket-shaped assembly is configurable in an expanded arrangement wherein the splines bow radially outwardly and in a collapsed arrangement, wherein the splines are arranged generally along the longitudinal axis of the catheter body. A far-field electrode is disposed in the interior of the expanded basket-shaped assembly.

In an aspect of the apparatus includes, the far-field electrode is disposed on a longitudinal axis of symmetry of the basket-shaped assembly.

According to still another aspect of the apparatus, the far-field electrode is spaced apart from the spline electrodes by at least 0.5 cm.

Yet another aspect of the apparatus includes a contraction wire for retracting and expanding the basket-shaped assembly. The contraction wire is attached to the distal extremity of the basket-shaped assembly and forms a longitudinal axis of symmetry thereof, and the far-field electrode is disposed on the contraction wire.

According to yet another aspect of the apparatus, sets of the spline electrodes of respective splines are equidistant from the proximal extremity of the basket-shaped assembly, and the far-field electrode is equidistant from corresponding members of the sets of the spline electrodes.

Still another aspect of the apparatus includes a distal electrode location sensor mounted at or distal to the distal extremity of the basket-shaped assembly, and a proximal electrode location sensor mounted at or proximal to the proximal extremity of the basket-shaped assembly, whereby, in use, coordinates of the distal electrode location sensor relative to those of the proximal electrode location sensor can be determined and taken together with known information pertaining to curvature of the splines of the basket-shaped assembly to determine locations of each of the spline electrodes.

According to an additional aspect of the apparatus each of the splines has a non-conductive outer surface on which one or more of the spline electrodes are mounted, the spline electrodes including ring electrodes.

According to another aspect of the apparatus wherein each of the splines includes an internal flexible wire and a non-conductive coveting over the flexible wire on which one or more of the spline electrodes are mounted, the spline electrodes including ring electrodes.

According to one aspect of the apparatus, the internal flexible wire includes nitinol.

According to a further aspect of the apparatus, the basket-shaped assembly has between three and five splines.

According to an additional aspect of the apparatus, the far-field electrode is a ring electrode.

There is further provided according to embodiments of the invention a method, which is carried out by inserting a catheter into a heart of a subject. The catheter has an elongated catheter body, and a basket-shaped assembly at the distal end of the catheter body. The basket-shaped assembly has a plurality of splines connected at its proximal extremity and its distal extremity, and a plurality of spline electrodes disposed on the splines. The basket-shaped assembly is configurable in an expanded arrangement wherein the splines bow radially outwardly and in a collapsed arrangement, wherein the splines are arranged generally along the longitudinal axis of the catheter body. A far-field electrode is disposed in the interior of the expanded basket-shaped assembly. The method is further carried out by expanding the basket-shaped assembly to contact at least one of the spline electrodes with a surface of the heart, thereafter receiving an intracardiac electrogram with the at least one of the spline electrodes and receiving a far-field electrogram with the far-field electrode, wherein the intracardiac electrogram has a near-field component and a far-field component. The method is further carried out by removing the far-field component from the intracardiac electrogram while retaining the near-field component by applying the far-field electrogram to the intracardiac electrogram to generate a modified intracardiac electrogram, and reporting the modified intracardiac electrogram.

According to an aspect of the method, removing the far-field component comprises subtracting the far-field electrogram from the intracardiac electrogram.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Figure 1:
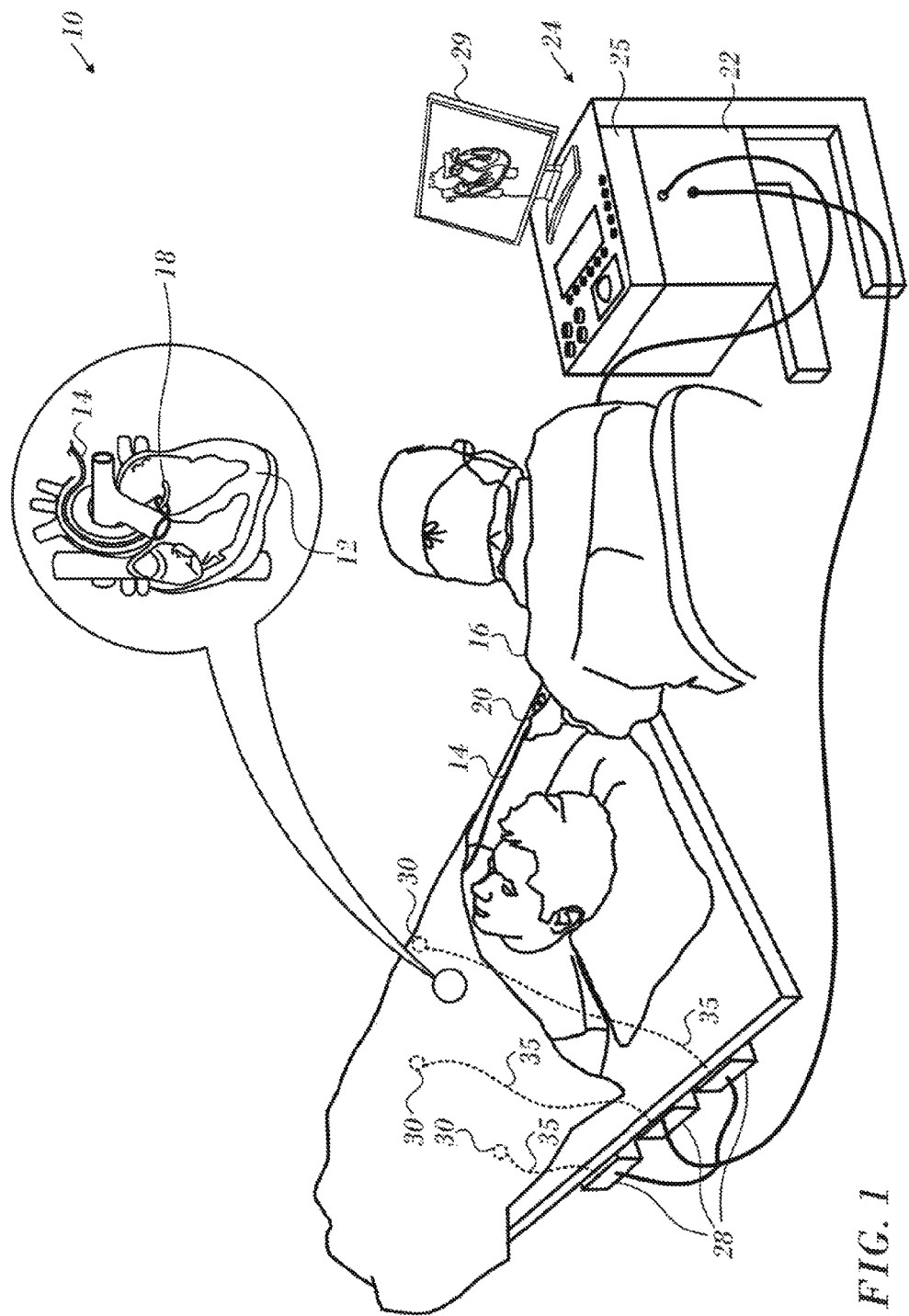
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Wire connections 35 link the console 24 with body surface electrodes 30 and other components of a positioning sub-system for measuring location and orientation coordinates of the catheter 14. The processor 22 or another processor (not shown) may be an element of the positioning subsystem. Catheter electrodes (not shown) and the body surface electrodes 30 may be used to measure tissue impedance at the ablation site as taught in U.S. Pat. No. 7,536,218, issued to Govari et al., which is herein incorporated by reference. Temperature sensors (not shown), typically a thermocouple or thermistor, may be mounted on ablation surfaces on the distal portion of the catheter 14 as described below.

The console 24 typically contains one or more ablation power generators 25. The catheter 14 may be adapted to conduct ablative energy to the heart using any known ablation technique, e.g., radiofrequency energy, ultra-sound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Figure 2:
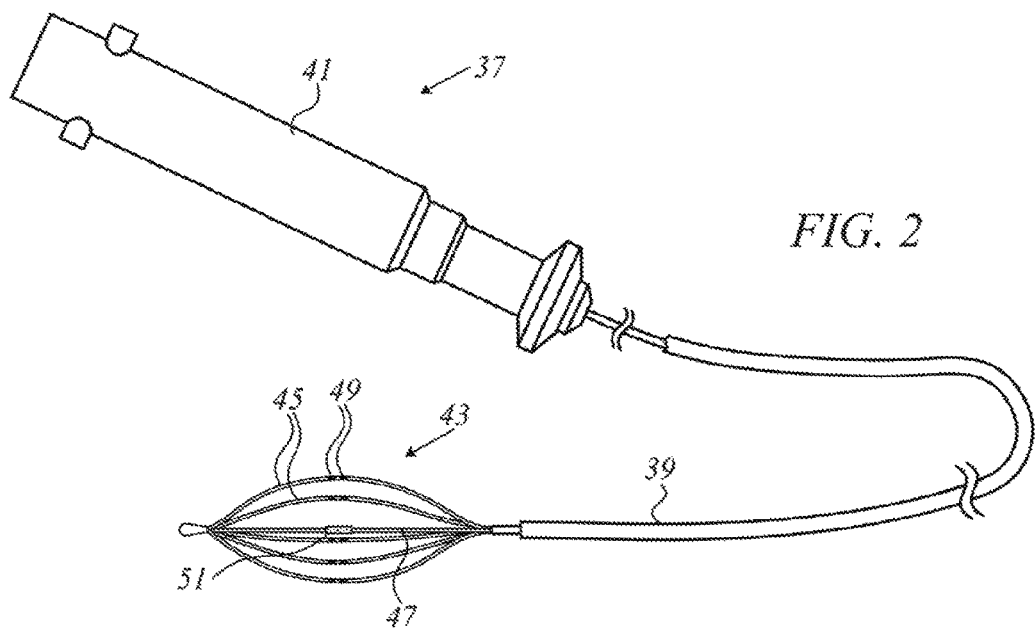
FIG. 2 is a perspective view of a catheter according to an embodiment of the invention.

Reference is now made to FIG. 2, which is a perspective view of a catheter 37 according to an embodiment of the invention, which is suitable for use with the system 10 (FIG. 1). The catheter 37 comprises an elongated shaft 39 having proximal and distal ends, a control handle 41 at the proximal end of the catheter body, and a basket-shaped electrode assembly 43 mounted at the distal end of the shaft 39.

The shaft 39 comprises an elongated tubular construction having a single, axial or central lumen (not shown), but can optionally have multiple lumens if desired. The shaft 39 is flexible, i.e., bendable, but substantially non-compressible along its length. The shaft 39 can be of any suitable construction and made of any suitable material. A presently preferred construction comprises an outer wall made of polyurethane or polyether block amide. The outer wall comprises an imbedded braided mesh of stainless steel or the like to increase torsional stiffness of the shaft 39 so that, when the control handle 41 is rotated, the distal end of the shaft 39 rotates in a corresponding manner.

The outer diameter of the shaft 39 is not critical, but is preferably no more than about 8 french, more preferably 7 french. Likewise the thickness of the outer wall is not critical, but is preferably thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The basket-shaped electrode assembly 43 is mounted to the distal end of the shaft 39. As shown in FIG. 2, the basket-shaped electrode assembly 43 comprises five splines 45 or arms mounted, preferably generally evenly-spaced, around a contraction wire 47, which is connected to the distal extremity of the electrode assembly 43, and which contracts, retracts and expands the electrode assembly 43 when a tractive or a pushing force is applied longitudinally to the contraction wire 47 as the case may be. The contraction wire 47 forms a longitudinal axis of symmetry for the electrode assembly 43. The splines 45 are all attached, directly or indirectly, to the contraction wire 47 at their distal ends, and to the shaft 39 at their proximal ends. When the contraction wire 47 is moved longitudinally to expand and contract the electrode assembly 43, in the expanded position the splines 45 are bowed outwardly and in the contracted position the splines 45 are generally straight. As will be recognized by one skilled in the art, the number of splines 45 can vary as desired depending on the particular application, so that the electrode assembly 43 has at least two splines, preferably at least three splines, and as many as eight or more splines. As used herein, the term "basket-shaped" in describing the electrode assembly 43 is not limited to the depicted configuration, but can include other designs, such as spherical or egg-shaped designs, that include a plurality of expandable arms connected, directly or indirectly, at their proximal and distal ends.

Each of the splines 45 comprises a flexible wire with a non-conductive covering on which one or more ring spline electrodes 49 are mounted. In a preferred embodiment, the flexible wires each comprise a flat nitinol wire and the non-conductive coverings each comprise a biocompatible plastic tubing, such as polyurethane or polyimide tubing. Alternatively, the splines 45 can be designed without the internal flexible wire if a sufficiently rigid nonconductive material is used for the non-conductive covering to permit expansion of the electrode assembly 43, so long as the spine has an outer surface that is non-conductive over at least a part of its surface for mounting of the ring spline electrodes 49.

Each of the ring spline electrodes 49 on the splines 45 is electrically connected to an appropriate mapping or monitoring system and/or source of ablation energy by means of an electrode lead wire (not shown). The electrode lead wires extend through the control handle 41, through a lumen in the shaft 39, into the non-conductive covering of corresponding splines 45, and attach to their corresponding ring spline electrodes 49 by any suitable method. The contraction wire 47 is provided with a far-field electrode 51, e.g., a cylindrical electrode, the function of which is described below. Additional details of the catheter 37 are described in the above-referenced U.S. Pat. No. 6,748,255.

The catheter 37 typically has multiple electrodes arranged on multiple flexible splines of the "basket." The catheter 37 is introduced into the heart 12 (FIG. 1) in a collapsed form, where the splines 45 are relatively close together. Once in the heart 12, the splines 45 may be formed into their expanded basket shape by the contraction wire 47, which holds distal ends of the splines 45, the splines 45 being pulled in a proximal direction.

Figure 3:
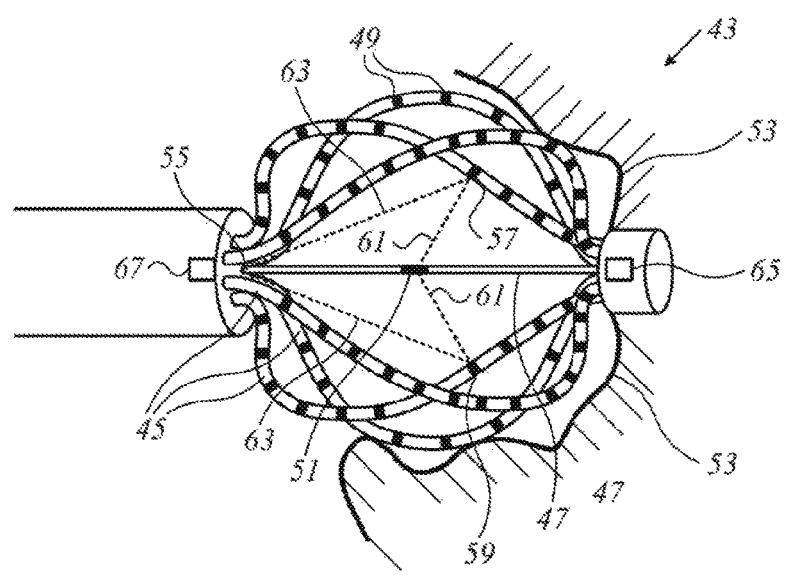
FIG. 3 is a detailed schematic view of an electrode assembly, in accordance with an embodiment of the invention.

Reference is now made to FIG. 3, which is a detailed schematic view of the electrode assembly 43 (FIG. 2), in accordance with an embodiment of the invention. In expanded form of the electrode assembly 43 at least a portion of the spline electrodes 49 of the splines 45 contact endocardial surface 53 of the heart 12 and acquire signals corresponding to electropotentials generated at their points of contact with the surface. However, since the spline electrodes 49 are in a conductive medium (the blood), in addition to the electropotentials from the points of contact the acquired signals also include far-field components from other regions of the heart 12.

The far-field components constitute an interfering signal on the endocardial surface electropotentials. To counteract the interference, embodiments of the present invention position the far-field electrode 51 on the contraction wire 47. In the expanded configuration of the electrode assembly 43, the far-field electrode 51 is located on the contraction wire 47 so as to be approximately equidistant from all corresponding spline electrodes 49, i.e., spline electrodes 49 that are equidistant from a fixed reference point on the long axis of the catheter, such as reference point 55 at the proximal end of the electrode assembly 43, and is prevented from contacting the surface of the heart by the splines. For example, electrodes 57, 59 are equidistant from reference point 55, and are also equidistant from the far-field electrode 51, as indicated by broken lines 61, 63, respectively. When the far-field electrode 51 is at least 0.5 cm removed from the spline electrodes 49 in the expanded configuration of the electrode assembly 43 it acquires a far-field signal, but not a near-field signal from the endocardial surface 53. However the signals acquired by the spline electrodes 49 have both a far-field and a surface (near-field) component. The far-field component signal x(t) acquired by the far-field electrode 51 is removed from signals e(t) acquired by the spline electrodes 49 so as to counteract the interference suffered by these electrodes, i.e., by subtraction of the signals: e(t)−x(t). Additionally or alternatively, removal of the far-field component may be accomplished using the teachings of copending, commonly assigned application Ser. Nos. 14/574,578, 14/585,828 and 62/093,773, the disclosures of which are herein incorporated by reference.

In some embodiments, the catheter 37 is provided with a distal electrode location sensor 65 mounted at or near the position where the distal ends of the splines are connected, and a proximal electrode location sensor 67 mounted at or near the proximal end of the electrode assembly 43, whereby, in use, the coordinates of the electrode location sensor 65 relative to those of the electrode location sensor 67 can be determined and taken together with known information pertaining to the curvature of the splines 45 to find the positions of each of the spline electrodes 49.

Figure 4:
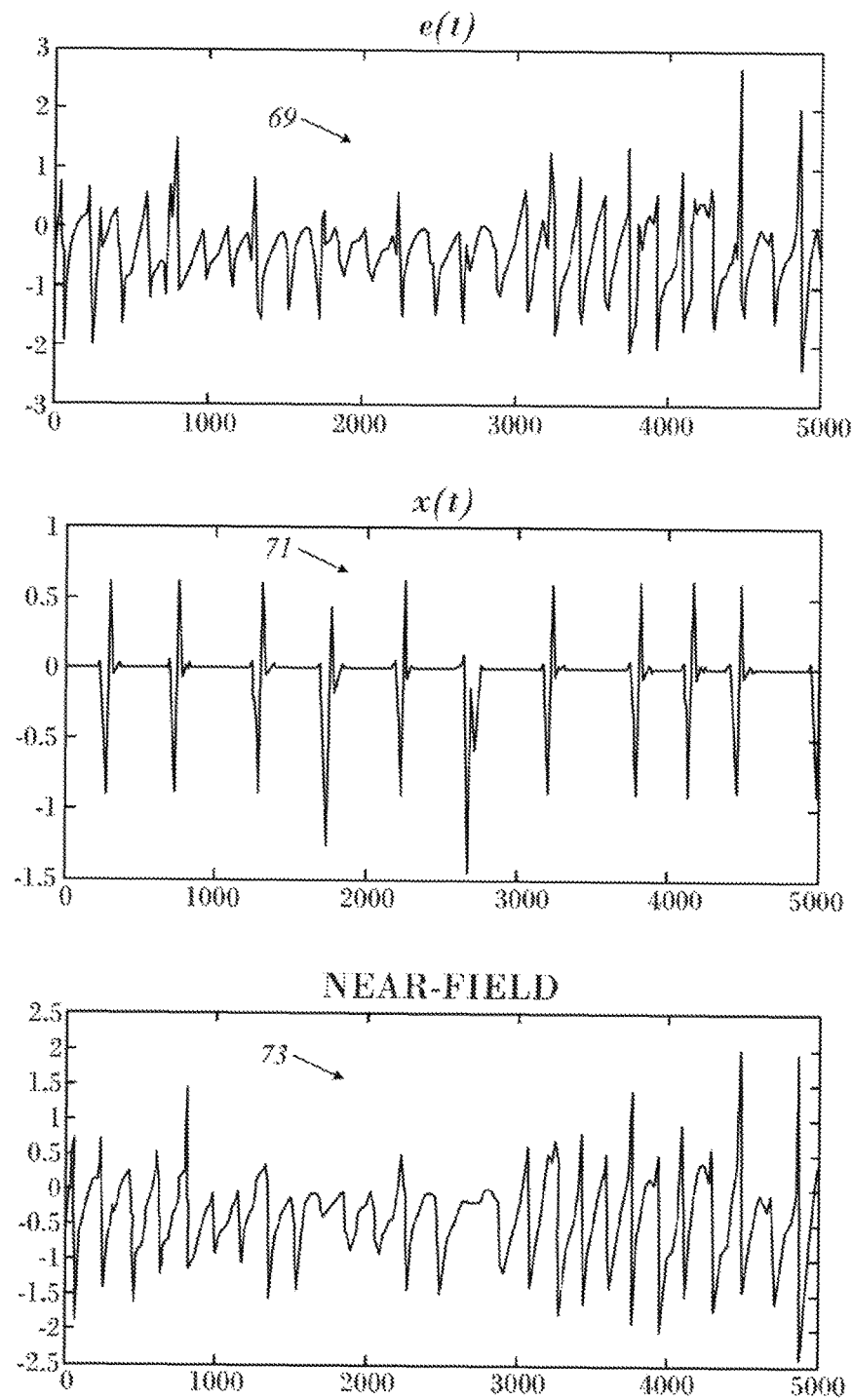
FIG. 4 is a prospective graph of signals that may be obtained using the arrangement shown in FIG. 3, in accordance with an embodiment of the invention.

Reference is now made to FIG. 4, which is a prospective graphical example of signals that may be obtained from a subject using the arrangement shown in FIG. 3, in accordance with an embodiment of the invention. Graph 69 shows an electrogram e(t) obtained from a unipolar or bipolar configuration of the spline electrodes 49. Graph 71 is a signal tracing x(t) of the far-field electrode 51, which may be a concurrent tracing. Graph 73 is a tracing of the signal obtained when the far-field component in the electrogram e(t) is removed by subtraction of the signal of graph 71 from the graph 69 or by application, mutatis mutandis, of the algorithms described in the above-noted application Ser. Nos. 14/574,578, 14/585,828 and 62/093,773.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus comprising:
   a catheter having an elongated catheter body, the catheter body having an interior, proximal end, a distal end and at least one lumen therethrough;
   a basket-shaped assembly at the distal end of the catheter body, the basket-shaped assembly having a longitudinal axis, a proximal extremity and a distal extremity and comprising a plurality of splines connected at the proximal extremity and the distal extremity, the splines comprising a plurality of spline electrodes, the basket-shaped assembly configurable in an expanded arrangement wherein the splines bow radially outwardly and in a collapsed arrangement, wherein the splines are arranged generally along the longitudinal axis of the catheter body;
   a contraction wire attached to the distal extremity of the basket assembly and slideably engaged within the elongated body, the contraction wire being configured to retract and or expand the basket-shaped assembly; and
   a far-field electrode disposed on the contraction wire and located in the interior of the expanded basket-shaped assembly, the far-field electrode being configured to detect far-field electrical activity that interferes with cardiac signal acquisition.

2. The apparatus according to claim 1, further comprising, wherein the far-field electrode is disposed on a longitudinal axis of symmetry of the basket-shaped assembly.

3. The apparatus according to claim 1, wherein the far-field electrode is spaced apart from the spline electrodes by at least 0.5 cm.

4. The apparatus according to claim 1, wherein sets of the spline electrodes of respective splines are equidistant from the proximal extremity of the basket-shaped assembly, and wherein the far-field electrode is equidistant from corresponding members of the sets of the spline electrodes.

5. The apparatus according to claim 1, further comprising a distal electrode location sensor mounted at or distal to the distal extremity of the basket-shaped assembly, and a proximal electrode location sensor mounted at or proximal to the proximal extremity of the basket-shaped assembly, whereby, in use, coordinates of the distal electrode location sensor relative to those of the proximal electrode location sensor can be determined and taken together with known information pertaining to curvature of the splines of the basket-shaped assembly to determine locations of each of the spline electrodes.

6. The apparatus of claim 1 wherein each of the splines has a non-conductive outer surface on which one or more of the spline electrodes are mounted, the spline electrodes comprising ring electrodes.

7. The apparatus of claim 1 wherein each of the splines comprises an internal flexible wire and a non-conductive covering over the flexible wire on which one or more of the spline electrodes are mounted, the spline electrodes comprising ring electrodes.

8. The apparatus of claim 7, wherein the internal flexible wire comprises nitinol.

9. The apparatus of claim 1, wherein the basket-shaped assembly has between three and five splines.

10. The apparatus according to claim 1, wherein the far-field electrode is a ring electrode.

* * * * *